(12) United States Patent
Kawakami et al.

(10) Patent No.: US 8,642,318 B2
(45) Date of Patent: Feb. 4, 2014

(54) ANTI-FATTY LIVER AGENT

(75) Inventors: Hiroshi Kawakami, Saitama (JP); Hiroaki Matsuyama, Saitama (JP); Masao Sato, Fukuoka (JP); Katsumi Imaizumi, Fukuoka (JP)

(73) Assignee: Megmilk Snow Brand Co., Ltd., Sapporo (JP)

( * ) Notice: Subject to any disclaimer, the term of this patent is extended or adjusted under 35 U.S.C. 154(b) by 748 days.

(21) Appl. No.: 12/375,097

(22) PCT Filed: Jul. 24, 2007

(86) PCT No.: PCT/JP2007/000791
§ 371 (c)(1),
(2), (4) Date: Dec. 10, 2009

(87) PCT Pub. No.: WO2008/012947
PCT Pub. Date: Jan. 31, 2008

(65) Prior Publication Data
US 2010/0129333 A1  May 27, 2010

(30) Foreign Application Priority Data
Jul. 25, 2006  (JP) ................................ 2006-201733

(51) Int. Cl.
*C12N 1/20* (2006.01)
(52) U.S. Cl.
USPC .................. 435/252.9; 424/93.45; 426/61
(58) Field of Classification Search
None
See application file for complete search history.

(56) References Cited

FOREIGN PATENT DOCUMENTS

| JP | 59-225120 | | 12/1984 |
|---|---|---|---|
| JP | 62-258323 | | 11/1987 |
| JP | 10072493 | * | 3/1998 |
| JP | 2003-252772 | | 9/2003 |
| JP | 2003252772 A | * | 9/2003 |
| JP | 2004-277296 | | 10/2004 |

OTHER PUBLICATIONS

Hamaguchi et al., Ann Intern Med., 2005, vol. 143, p. 722-728.*
Takeshi Yoshida et al. "*Lactobacillus gasseri* Hakkonyu ni yoru Shishitsu Taisha Chosetsu", Annual Meeting of JSBBA Koen Yoshishu, dated Mar. 3, 2007, p. 78.
Yoriko Iseda et al, "*Lactobacillus gasseri* Hakkonyu no Shishitsu Taisha Chosetsu Kko", Annual Meeting of JSBBA Koen Yoshishu, dated Mar. 3, 2007, p. 135.
Inernational Search Report issued on Aug. 9, 2007, Application No. PCT/JP2007/000791.
Lee, H.Y. et al., Human originated bacteria, *Lactobacillus rhamnosus* PL60, produce conjugated linolelic acid and show anti-obesity effects in diet-induced obese mice, Biochim Biophys Acta, May 20, 2006, vol. 1761, No. 7, p. 736-744.
Japanese Office Action issued Apr. 11, 2012 by the Japanese Patent Office in corresponding Japanese Patent Application No. 2006-201733, 4 pages.
International Bureau of WIPO issued a International Preliminary Report on Patentability dated Jul. 24, 2007, Application No. PCT/JP2007/00791.

* cited by examiner

*Primary Examiner* — Kade Ariani
(74) *Attorney, Agent, or Firm* — Young & Thompson

(57) ABSTRACT

Disclosed is an anti-fatty liver agent comprising a cell and/or a culture obtained by culturing a lactic acid bacterium belonging to *Lactobacillus gasseri* as an active ingredient. Also disclosed is a pharmaceutical agent having an anti-fatty liver activity or an anti-fatty liver beverage/food comprising a cell and/or a culture obtained by culturing a lactic acid bacterium belonging to *Lactobacillus gasseri* as an active ingredient.

11 Claims, No Drawings

ANTI-FATTY LIVER AGENT

TECHNICAL FIELD

The present invention relates to an anti-fatty liver agent containing a culture and/or a bacterial body obtained by cultivating a lactic acid bacterium belonging to *Lactobacillus gasseri* as an active ingredient. The present invention also relates to a pharmaceutical agent having an anti-fatty liver activity containing a culture and/or a bacterial body obtained by cultivating a lactic acid bacterium belonging to *Lactobacillus gasseri* as an active ingredient. The present invention further relates to an anti-fatty liver beverage/food containing a culture and/or a bacterial body obtained by cultivating a lactic acid bacterium belonging to *Lactobacillus gasseri* as an active ingredient.

BACKGROUND ART

Fatty liver refers to a state where fat has excessively accumulated in liver (hepatocyte). With fat accumulation, various symptoms such as anorexia, weight loss, and fatigue appear. The mechanism of fatty liver development remains unknown, but the mechanism has been considered to be as follows on the basis of previous researches. In other words, the liver serves a crucial role in the metabolism and transfer of fat and fat balance in the liver is maintained at a constant equilibrium state in normal conditions. Liver neutral fat is derived from fatty acids in chylomicron from meal, free fatty acids mobilized from peripheral fat tissues, and fatty acids freshly synthesized in the liver. One part of fatty acids, which were thus freshly synthesized in the liver or transferred to the liver, is subject to oxidative destruction in the liver. Another part of fatty acids is esterified in a liver microsome and converted to a neutral fat. The neutral fat is bound to protein and secreted into blood stream in a form of lipoprotein. Liver neutral fat is maintained at an equilibrium state with metabolic turnover in a relatively rapid manner. However, if changes occur, which disturb the equilibrium in the liver, that is, cause the disequilibrium between the production and utilization amounts of neutral fat in the liver, fatty liver develops. In theory, the causes of fatty liver are considered as follows: increased fat synthesis in the liver; decreased fatty acid oxidation in the liver; increased fat mobilization from peripheral fat to the liver; and decreased fat transfer from the liver to the peripheral. As the causes of those abnormalities, there are given a number of causes such as: oxygen deficiency due to anemia gravis, circulatory disorder, etc.; endocrinopathy due to Graves' disease, etc.; metabolic disease due to child constitution, etc.; pancreatic disease; malnutrition; exogenous toxic agents or chemicals due to alcohol, phosphorus, mushroom poison, etc.; endogenous toxic agents due to chronic infection, etc.; fat and carbohydrate meal property; and small intestine bypass surgery. Fatty liver has been also considered as a factor of severe diseases such as chronic hepatitis and liver cirrhosis, and hence the treatment and prevention of the fatty liver has been a critical issue.

With respect to a method of preventing and treating fatty liver, for example, the following technologies have been known: a liver fat accumulation inhibitory composition characterized by containing an effective amount of conjugated diene linoleic acids together with a carrier for medicinal preparations or foods (for example, Patent Document 1); a fat and oil composition characterized by mixing fat and oil containing highly unsaturated fatty acids with egg yolk lipid containing about 25 to about 70% by weight of phospholipid (for example, Patent Document 2); a composition containing at least one kind of amino acids having a glucagon secreting activity, at least one kind of xanthine derivatives, and at least one kind of thiamine compounds (for example, Patent Document 3); a fraction of crude soybean lecithin having a function to suppress synthesis of neutral fat in liver, obtained by fractionating a crude soybean lecithin produced in the production process of fat and oil from soybean using organic solvents, adsorbents, ion-exchange resins, and the like, and a beverage/food, an animal feed, or a pharmaceutical agent obtained by mixing a known raw material with the crude soybean lecithin fraction (for example, Patent Document 4); a lipid metabolism improving agent and a hepatic disorder suppressing agent containing an extract of *Phyllanthus niruri* extracted with organic solvents or water as an active ingredient (for example, Patent Document 5); an agent for suppressing lipid increase containing xyloglucan as an active ingredient (for example, Patent Document 6); a composition, migrating from buckwheat flour to a liquid layer and separated in a mixture of the buckwheat flour and water (for example, Patent Document 7); an improver for lipid metabolism containing α-curcumene which is a bisabolane-type sesquiterpenoid isolated from *Curcuma xanthorrhiza Roxb.* as an active ingredient (for example, Patent Document 8); a fatty liver suppressing agent containing one or two or more kinds of triglycerides selected from tristearin, 1-stearyldipalmitin, 2-stearyldipalmitin, 1-palmitodistearin, and 2-palmitodistearin as an active ingredient (for example, Patent Document 9); an improver for liver function containing docosahexaenoic acid (referred to as DHA) as an active ingredient (for example, Patent Document 10); and an alcoholic fat liver suppresser containing hemicellulose obtained by removing starch, protein, and the like from corn wheat bran and extracting the residual part with an alkali and/or partially decomposed product of hemicellulose obtained by further treating the hemicellulose with xylanase as an active ingredient (for example, Patent Document 11) However, an effective method for prevention and treatment of fatty liver has not been established yet, a novel active ingredient with safety and high effectiveness and a composition containing the ingredient, and further a novel food and pharmaceutical agent using the ingredient and the composition have been desired.

For *Lactobacillus gasseri* which is a lactic acid bacterium, for example, the findings on the following have been obtained: an immunopotentiating agent (for example, Patent Document 12); an agent for preventing infection with pathogen (for example, Patent Document 13); an agent for preventing serum cholesterol level from increasing (for example, Patent Document 14); an antioxidant (for example, Patent Document 15); an agent for prevention, improvement, and treatment of diabetic complication (for example, Patent Document 16); and a medicine for preventing and treating inflammatory intestinal disease and allergic intestinal syndrome (for example, Patent Document 17). Patents for *Lactobacillus gasseri* have been published, but its influences on liver function and tissue characteristics have not been known at all.

Patent Document 1: JP 11-79987 A
Patent Document 2: JP 10-237480 A
Patent Document 3: JP 10-158170 A
Patent Document 4: JP 10-84879 A
Patent Document 5: JP 9-241176 A
Patent Document 6: JP 9-224608 A
Patent Document 7: JP 9-183735 A
Patent Document 8: JP 7-149628 A
Patent Document 9: JP 6-279278 A
Patent Document 10: JP 5-339154 A
Patent Document 11: JP 5-43470 A Patent Document 12: JP 2006-69993 A
Patent Document 13: JP 2005-225841 A
Patent Document 14: JP 2003-306436 A
Patent Document 15: JP 2003-253262 A
Patent Document 16: JP 2003-252770 A
Patent Document 17: JP 2003-95963 A

DISCLOSURE OF THE INVENTION

Problem To Be Solved By the Invention

It is an object of the present invention to provide an anti-fatty liver agent having functions for prevention, improvement, and treatment of fatty liver, a pharmaceutical agent having an anti-fatty liver activity, and an anti-fatty liver beverage/food.

Means For Solving the Problems

The inventors of the present invention have studied a variety of fermented milk. As a result, the inventors have found that a culture and a bacterial body of a lactic acid bacterium isolated from a fermented food and a lactic acid bacterium derived from human, inter alia, a lactic acid bacterium belonging to *Lactobacillus gasseri* gives the inhibition of fatty liver formation, and thus succeeded in solving the above-mentioned problems.

In other words, the present invention relates to an anti-fatty liver agent containing a bacterial body and a culture obtained by cultivating a lactic acid bacterium belonging to *Lactobacillus gasseri* as an active ingredient. The present invention further relates to a pharmaceutical agent having an anti-fatty liver activity and an anti-fatty liver beverage/food, containing a bacterial body and a culture obtained by cultivating a lactic acid bacterium belonging to *Lactobacillus gasseri* as an active ingredient.

Effects of the Invention

According to the present invention, there can be provided the anti-fatty liver agent, the pharmaceutical agent having an anti-fatty liver activity, and the anti-fatty liver beverage/food, containing a culture and/or a bacterial body obtained by cultivating a lactic acid bacterium belonging to *Lactobacillus gasseri* as an active ingredient. The anti-fatty liver agent of the present invention has extremely low toxicity and an adverse side effect. Therefore, it is particularly useful as a food material.

BEST MODE FOR CARRYING OUT THE INVENTION

The present invention has been made to solve the above-mentioned problems. The inventors of the present invention, in screening a targeted lactic acid bacterium, has newly established criteria as described below and selected a strain which meets the purpose. In other words, the inventors have established the following conditions, for a number of lactic acid bacteria derived from a fermented food and human, such as: having high gastric acid resistance; growing well in low pH conditions; suppressing the elevation of serum cholesterol level; exhibiting high colonization characteristics to human intestine; exhibiting affinity to human intestinal cells; having bile acid resistance; having cholesterol adsorptivity; having bile acid adsorptivity; and having high survivability as well as excellent flavors and physical properties in food application. The inventors have intensively studied the selection for a bacterial strain based on the above conditions. No bacterial strain of *Lactobacillus gasseri* satisfying such conditions had been known yet.

As a result of screening under the above conditions, the following bacterial strains were able to be selected as bacterial strains which met those conditions. Those bacterial strains have been deposited to the National Institute of Advanced Industrial Science and Technology under the following deposit numbers.

That is, the strains include *Lactobacillus gasseri* SBT10801 (FERM P-18137), *Lactobacillus gasseri* SBT1703 (FERN P-17785), *Lactobacillus gasseri* SBT10241 (FERM P-17786), *Lactobacillus gasseri* SBT0274 (FERN P-17784), *Lactobacillus gasseri* SBT10239 (FERM P-16639), and *Lactobacillus gasseri* SBT2055 (FERM P-15535).

*Lactobacillus gasseri* SBT2055(FERM BP-15535) deposited under the terms of the Budapest Treaty with International Patent Organism Depository, National Institute of Advanced Industrial Science and Technology, address: AIST Tsukuba Central 6, 1-1, Higashi 1-Chome, Tsukuba-shi, Ibaraki-ken, 305-8566 JAPAN, on Mar. 27, 1996, under accession number FERM BP-10953, formerly under FERM BP-15535.

*Lactobacillus gasseri* SBT0274(FERM BP-17784) deposited under the terms of the Budapest Treaty with National Institute of Advanced Industrial Science and Technology, address: AIST Tsukuba Central 6, 1-1, Higashi 1-Chome, Tsukuba-shi, Ibaraki-ken, 305-8566 JAPAN, on Mar. 15, 2000, under accession number FERM BP-11039, formerly under FERM BP-17784.

In addition, those bacterial strains have a high affinity to human intestinal cells. In oral administration, the strains can be delivered alive into the intestine and be resident in the intestine for extended periods. Further, in the present invention, any strain other than the deposited strains as described above may be also used as long as the strain is a bacterial strain of *Lactobacillus gasseri* separated from human and a fermented food and exhibits the above-mentioned activity.

Then, there is given a method of cultivating those lactic acid bacteria. As a medium for *Lactobacillus gasseri* of the present invention, a variety of media can be utilized, such as a milk medium or a medium containing a milk constituent, or a semi-synthetic medium without the milk constituent. The example of such a medium may include a reduced skim milk medium obtained by reducing and heat-sterilizing skim milk. The cultivation is performed with static cultivation or neutralizing cultivation in which a pH is adjusted to a constant value. However, the cultivation method is not particularly limited thereto as long as the method satisfies the condition in which the bacteria grow up well.

In the present invention, there is contained a culture and/or a bacterial body obtained as described above as an active ingredient. Further, dry powder may be contained as an active ingredient. It is preferred that those cultures and/or bacterial bodies be dried with lyophilization since drying can be performed without the degeneration of the bacterial bodies. However, a method involving the addition of heat such as spray drying may be also applied.

Then, it is desirable that those active ingredients be orally ingested. Further, those powders can be mixed with appropriate excipients such as lactose and orally ingested in the forms of powders, tablets, pills, capsules, granules, or the like. The ingestion amount is appropriately determined in view of symptom, age, and the like of each of ingestion subjects individually. Generally, in the case of an adult, the ingestion amount may be 0.5 to 50 g as a dry substance per day per adult and ingested in several portions daily. Further, examples of the beverage/food in the present invention may include a yogurt produced with lactic acid fermentation using a bacterial strain of *Lactobacillus gasseri* as described above.

The anti-fatty liver agent, the pharmaceutical agent having an anti-fatty liver activity, and the anti-fatty liver beverage/food of the present invention, containing a culture and/or a bacterial body obtained by cultivating a lactic acid bacterium belonging to *Lactobacillus gasseri* as an active ingredient, can be expected to have prevention and improvement effects for fatty liver caused by a variety of factors, for example, fatty liver due to alcohol ingestion, fatty liver due to excess ingestion of energy, fatty liver due to the decrease of a fat degradation ability in liver, fatty liver due to the acceleration of fat synthesis in liver, and fatty liver due to the acceleration of fat absorption in small intestine. Accordingly, they can be utilized as a beverage/food material for maintaining and promoting health. Further, the decreased liver function due to fatty liver generally leads to significant decrease in physical fitness. Therefore, the prevention and improvement of fatty liver contributes to the maintenance, promotion, and retrieval of physical fitness, and hence the food composition of the present invention can be also utilized as a healthy food composition for the maintenance, promotion, and retrieval of physical fitness.

Hereinafter, as the lactic acid bacterium used in the present invention, a test example using *Lactobacillus gasseri* SBT2055 (FERM P-15535) (Hereinafter referred to as SBT2055) is described. In addition, the taxonomical properties of the bacterium and effects of the bacterium in vitro and in vivo are described in detail.

TEST EXAMPLE 1

(Identification of Strain SBT2055)
1. Taxonomical Properties
(1) Form of bacterium
The results of anaerobic culture at 37° C. for 48 hours using a LBS agar plate medium are described.
Form: *Bacillus*
Size: 0.5 to 1×3 to 4 μm
Many of them chained each other.
(2) Gram stain: positive
(3) Morphology of colonies
Form: circle
Circumference: wave-like
Size: 2- to 3-mm in diameter
Color tone: white
Surface: smooth
(4) Sporulation: negative
(5) Gas production: none
(6) Motility: none
(7) Catalase activity: negative
(8) Coagulability of skim milk: coagulation
(9) Gelatin liquefaction: none
(10) Nitrate reductivity: none
(11) Production of indole: none
(12) Production of hydrogen sulfide: none
 2. Fermentative Properties of Sugar
Results of fermentative properties of sugar determined by a commercially available kit for identifying bacteria (Api 50CH, BioMérieux) are described below.
Glycerol –
Erythritol –
D-arabinose –
L-arabinose +
Libose –
D-xylose –
L-xylose –
Adnitol –
β-methyl-D-xyloside –
Galactose +
D-glucose +
L-fluctose +
D-mannose +
L-sorbose –
Rhamnose –
Dulcitol –
Inositol –
Mannitol –
Sorbitol –
α-methyl-D-mannoside –
α-methyl-D-glucoside –
N-acetyl-glucosamine +
Amygdalin +
Arbutin +
Esculin +
Salicin +
Cellobiose +
Maltose +
Lactose +
Melibiose –
Saccharose +
Trehalose +
Inulin –
Melezitose –
D-raffinose –
Amidone –
Glycogen –
Xylitol –
β-gentiobiose +
D-turanose –
D-lyxose –
D-tagatose +
D-arabitol –
L-arabitol –
Gluconate –
2-keto-gluconate –
5-keto-gluconate –
(+ represents the case where fermentative property was found and – represents the case where no fermentative property was found)

The above taxonomical properties represent typical properties of *Lactobacillus acidophilus* complex.
 3. Homology
An identification test was performed by a DNA homology test.

DNAs of a type strain of *Lactobacillus*, a test bacterium strain SBT2055, and *Escherichia coli* as a control described below were extracted and purified.
Test bacterium: strain SBT2055
Type strain: *Lactobacillus acidophilus* strain JCM1132
 *Lactobacillus crispatus* strain JCM1185
 *Lactobacillus gallinarum* strain JCM2011
 *Lactobacillus amylovorus* strain JCM1126
 *Lactobacillus gasseri* strain JCM1131
 *Lactobacillus johnsonii* strain JCM2021
 *Escherichia coli*
DNA homology between the strains SBT2055 was set to be 100% and DNA homology between the strain SBT2055 and *Escherichia coli* was set to be 0%. Under such a setting, DNA homology between the strain LG2055 and each of type strains was investigated using DNA hybridization method. As a result, the strain SBT2055 had a homology of 90% or more to Lactobacillus gasseri strain JCM1131, and hence the strain SBT2055 was identified as Lactobacillus gasseri.

TEST EXAMPLE 2

(Intestinal Permeability and Intestinal Colonization Characteristics in Human)

The starter of the strain SBT2055 was inoculated in an amount of 4% with respect to milk containing 9.5% solids-not-fat and 3.0% milk fat and fermented at 39° C. for 4 hours. Every day for 4 weeks, 42 healthy adult volunteers were allowed to ingest 100 g of the resulting fermented milk once daily and changes in enterobacteria were observed. During the test period, the evaluation was performed under free ingestion of meal except that the ingestion of foods, oligosaccharides, and chemicals affecting enterobacteria was prohibited. The strain SBT2055, which had not been detected before the test, was detected from all the subjects after 4 weeks. Accordingly, it has been found that the strain SBT2055 has high intestinal colonization characteristics.

TEST EXAMPLE 3

(Preparation for Lactobacillus Gasseri Skim Milk Culture)

To stimulate the strain SBT2055, passage cultivation was performed in three generations or more at 37° C. for 16 hours in an 11.55% skim milk medium supplemented with 0.5% yeast extract (manufactured by Asahi Breweries, Ltd.) subjected to sterilization treatment at 115° C. for 20 minutes. The resultant was inoculated in an amount of 3% with respect to the same medium and cultivated at 37° C. for 16 hours. The resulting culture was lyophilized and then pulverized in a mortar.

TEST EXAMPLE 4

(Measurement of Liver Lipid)

Four-week-old SD rats were preliminarily fed for 1 week and then divided into a group which ingested a feed containing 20% Lactobacillus gasseri skim milk culture prepared in Test Example 3 (gasseri culture group) and a group which ingested a feed containing 20% skim milk (control group). Lipid content was set to be 10%. For the ingestion, pair-feeding started in the middle of feeding, and the rats were fed for 4 weeks under the conditions of free drinking, 12-hour light cycle, and room temperature of 21 to 23° C. After 4 weeks of ingestion, without a fasting period, the rats were sacrificed by collecting the blood from the aorta abdominalis to provide the liver and serum. According to the Folch method (Folch, J. Biol. Chem., 226, 497-506, 1957), liver lipid was extracted with a chloroform:methanol=2:1 (V/V) solution and washed with water, followed by the quantification of the amounts of triglyceride, phospholipid, andcholesterol. The triglyceride, phospholipid, and cholesterol were assayed using an acetyl acetone method (Triglyceride Test Wako, manufactured by Wako Pure Chemical Industries, Ltd.), a permanganate-incineration method (Phospholipid Test Wako, manufactured by Wako Pure Chemical Industries, Ltd.), an enzyme method (Detaminer TC555, manufactured by Kyowa Medex Co., Ltd.), respectively.

Table 1 shows the results of liver lipid measurement. For ingestion amount, final weight and defecation amount, there were found no differences between the groups. For liver weight, serum lipid, liver cholesterol, and liver phospholipid, there were also no differences between the groups. However, liver neutral lipid (TG) amount was significantly low in the gasseri culture group.

TABLE 1

| | Control group | Gasseri culture group | |
|---|---|---|---|
| Neutral lipid | 44.58 ± 5.21 | 25.63 ± 3.25 | *p < 0.05 |
| Cholesterol | 2.92 ± 0.19 | 2.96 ± 0.27 | |
| Phospholipid | 26.82 ± 0.48 | 27.71 ± 0.73 | |

TEST EXAMPLE 5

(Measurement of Liver Fatty Degeneration)

Ten-week-old female C57BL/6J mice (Crj:CD-1 (ICR), manufactured by Charles River Laboratories Japan Inc.) were divided into 5 animals/group. Control group A was fed with a purified feed which was diet containing high fat and high sugar (manufactured by Oriental Yeast Co., ltd.), and control group B was fed with a feed obtained by adding 8% soybean oil as fat content to a normal mixed feed for a growth period from which fat was removed (AIN-93G: manufactured by Oriental Yeast Co., ltd.) (normal diet). The gasseri culture group was fed with a feed in which protein and carbohydrate portions of the purified feed which was diet containing high fat and high sugar as described above were replaced by Lactobacillus gasseri skim milk culture prepared in Test Example 3. Each of the groups was fed with a test feed or a control feed for 4 weeks. Following the fasting treatment for about 16 hours after the final day of feeding, the mice in each group were sacrificed by bleeding under ether anesthesia to excise their livers. After the formalin fixation of the liver, paraffin sections of the liver were made by a common method and subjected to hematoxylin and eosin staining followed by the search for pathological tissues using a light microscope. The degree of liver fatty degeneration was graded into 5 scales (−, ±, +, ++, +++), and the evaluation was carried out based on the number of individuals in each scale.

Table 2 shows the results of evaluation. In the group fed with diet containing high fat and high sugar (control group A), an image was confirmed in which fat accumulated in the liver to thereby become fatty liver. In the group fed with normal diet (control group B), such an image was not confirmed. In the gasseri culture group, an image was confirmed in which fat accumulation was suppressed.

TABLE 2

| | Frequency of liver fatty degeneration | | | | |
|---|---|---|---|---|---|
| | − | ± | + | ++ | +++ |
| Control group A | 0 | 0 | 1 | 4 | 1 |
| Control group B | 6 | 0 | 0 | 0 | 0 |
| Gasseri culture group | 2 | 2 | 2 | 0 | 0 |

Hereinafter, the present invention will be specifically described with reference to Examples. However, the present invention is not limited to those Examples.

EXAMPLE 1

The strain SBT2055 was inoculated in an amount of 3% with respect to a 10% reduced skim milk medium (heated at 121° C. for 10 minutes) and cultivated at 37° C. for 64 hours. The culture was lyophilized and then powdered to prepare an anti-fatty liver agent of the present invention.

EXAMPLE 2

A yogurt mix was prepared by heating fresh milk added with 2% skim milk at 100° C. for 10 minutes and cooled to 20°

C. After that, the strain SBT2055 was inoculated in an amount of 5% with respect to the yogurt mix and cultivated at 20° C. for 24 hours. The yogurt mix after the completion of cultivation was filled into a paper cup and cooled to afford an anti-fatty liver yogurt of the present invention.

EXAMPLE 3

The strain SBT2055 was inoculated in an amount of 3% with respect to a whey medium supplemented with 0.5% yeast extract and 0.1% trypticase peptone, and cultivated at 37° C. for 64 hours. After the cultivation, a bacterial body was removed with centrifugation. The resulting supernatant solution was added with ice-cold ethanol so as to have a final concentration of 50% to afford a precipitate. The precipitate was dissolved in 0.2 N NaCl, and the above-mentioned ethanol precipitation was repeated further three times to afford about 500 mg of precipitate per (culture). The mixing of 1 g of the culture and 5 g of lactose was carried out, following which the resultant was formed into a shape of granules and dried to afford anti-fatty liver granules of the present invention.

EXAMPLE 4

The strain SBT2055 was inoculated in an amount of 3% with respect to 5 L of MRS liquid media (manufactured by Difco Laboratories). After the inoculation, static cultivation was performed at 37° C. for 18 hours. After the completion of cultivation, the culture was centrifuged at 7,000 rpm for 15 minutes to afford an enriched bacterial body in an amount of 1/50 with respect to the culture media. The enriched bacterial body was then mixed in an equal amount with a dispersion medium containing 10% by weight of skim milk powders and 1% by weight of sodium glutamate. The resultant was adjusted to pH 7 followed by the lyophilization. The resulting lyophilizate was powdered through a 60-mesh sieve to afford an anti-fatty liver lyophilized bacterial powder of the present invention.

EXAMPLE 5

According to the provision of General Rules for Preparations "Powders" in the Guide to Japanese Pharmacopoeia, 13th edition, 1 g of lyophilized bacterial powder of the strain SBT2055 obtained in Example 4 as described above was added with 400 g of lactose (Japanese Pharmacopoeia) and 600 g of potato starch (Japanese Pharmacopoeia) and homogeneously mixed to produce anti-fatty liver powders of the present invention.

EXAMPLE 6

Skim milk was sterilized at 80 to 85° C. for 25 minutes, following which it was homogenized and cooled. The resultant was added with 3.5% pure culture of the strain SBT2055 as a starter and fermented at 37 to 40° C. for 16 hours to afford sour milk containing lactic acid in an amount of 2% (a culture in a skim milk medium). Then, the culture was cooled to 5° C. while a generated curd was pulverized, resulting in sour milk.

Separately, a sugar solution containing an appropriate amount of acidulants, flavors, and pigments other than 15% sucrose was formulated, homogenized, sterilized at 70 to 80° C. for 25 minutes, and then cooled to 5° C. to provide a sugar solution. Thus obtained sour milk and sugar solution were mixed at a proportion of 35 to 65 to afford an anti-fatty liver sour milk beverage of the present invention.

EXAMPLE 7

40 g of the lyophilized powder of the culture in the skim milk medium obtained in Example 1 as described above were added to 40 g of vitamin C or 40 g of a mixture of vitamin C and citric acid in the same amount, 100 g of granulated sugar, and 60 g of a mixture of corn starch and lactose in the same amount, and the resultant was mixed sufficiently. The mixture was put into a package, and 150 packages of anti-fatty liver nutritious and healthy foods shaped into a stick of the present invention having a weight of 1.5 g per package were produced.

The invention claimed is:

1. A method of treating fatty liver in a subject in need thereof, comprising administering to the subject an effective amount of *Lactobacillus gasseri* culture.

2. The method of claim 1, comprising administering to the subject a food or beverage comprising the *Lactobacillus gasseri* culture.

3. The method of claim 1, wherein the *Lactobacillus gasseri* is any one of *Lactobacillus gasseri*SBT2055 (FERM P-15535), and, *Lactobacillus gasseri* SBT0274 (FERM P-17784).

4. The method of claim 1, wherein the *Lactobacillus gasseri* culture is administered to the subject orally.

5. The method of claim 1, wherein the effective amount of *Lactobacillus gasseri* culture administered to the subject is 0.5 to 50 g dry weight per day.

6. The method of claim 2, wherein the food or beverage is a yogurt fermented by *Lactobacillus gasseri*.

7. A method for reducing triglyceride levels in the liver of a subject having fatty liver disease, comprising administering to the subject an effective amount of *Lactobacillus gasseri* culture comprising *Lactobacillus gasseri* SBT2055 (FERM P-15535.

8. A method for reducing the amount of liver fat in a subject having fatty liver disease, comprising administering to the subject an effective amount of *Lactobacillus gasseri* culture comprising *Lactobacillus gasseri* SBT2055 (FERM P-15535.

9. The method of claim 7, wherein the *L. gasseri* SBT2055 culture is a milk culture and the effective amount administered is 0.5 to 50 g dry weight per day.

10. The method of claim 8, wherein the *L. gasseri* SBT2055 culture is a milk culture and the effective amount administered is 0.5 to 50 g dry weight per day.

11. The method of claim 1, wherein the *L. gasseri* culture is a milk culture.

* * * * *

UNITED STATES PATENT AND TRADEMARK OFFICE
CERTIFICATE OF CORRECTION

PATENT NO. : 8,642,318 B2
APPLICATION NO. : 12/375097
DATED : February 4, 2014
INVENTOR(S) : Kawakami et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1078 days.

Signed and Sealed this

Twenty-ninth Day of September, 2015

Michelle K. Lee
*Director of the United States Patent and Trademark Office*